US008261914B2

(12) United States Patent
Hooyman et al.

(10) Patent No.: US 8,261,914 B2
(45) Date of Patent: Sep. 11, 2012

(54) PACKAGE OF DISPOSABLE ABSORBENT PANTS

(75) Inventors: Thomas R. Hooyman, Combined Locks, WI (US); Jared M. Mackrory, Provo, UT (US); Amanda J. Simon, Oshkosh, WI (US); Gregory J. Fries, Hubertus, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 300 days.

(21) Appl. No.: 12/700,981

(22) Filed: Feb. 5, 2010

(65) Prior Publication Data
US 2011/0192749 A1    Aug. 11, 2011

(51) Int. Cl.
B65D 73/00    (2006.01)
(52) U.S. Cl. ........................................ 206/494; 206/440
(58) Field of Classification Search ................ 206/440, 206/459.5, 494, 497, 499, 812; 604/385.01, 604/385.201, 385.24, 385.25
See application file for complete search history.

(56) References Cited

U.S. PATENT DOCUMENTS

| 4,966,286 A * | 10/1990 | Muckenfuhs | 206/494 |
| 2001/0045367 A1 * | 11/2001 | Bisbal et al. | 206/494 |
| 2004/0102748 A1 | 5/2004 | Hirotsu | |
| 2004/0129592 A1 * | 7/2004 | Otsubo | 206/440 |
| 2004/0168947 A1 * | 9/2004 | McDonald | 206/494 |
| 2004/0195137 A1 * | 10/2004 | Otsubo | 206/494 |
| 2004/0211696 A1 * | 10/2004 | Underhill et al. | 206/494 |
| 2007/0012519 A1 | 1/2007 | Angielski | |
| 2007/0267322 A1 | 11/2007 | Kishida et al. | |
| 2008/0234643 A1 * | 9/2008 | Kaneda | 604/358 |

FOREIGN PATENT DOCUMENTS

| JP | 10-043237 A | 2/1998 |
| JP | 10-95481 * | 4/1998 |
| JP | 2000024029 A | 1/2000 |
| JP | 2000024230 A | 1/2000 |

* cited by examiner

Primary Examiner — Luan K Bui
(74) Attorney, Agent, or Firm — H. Michael Kubicki; R. Joseph Foster, III

(57) ABSTRACT

A package of disposable pants comprises a housing portion comprising a front panel comprising a front transparent window. The package further includes a plurality of disposable absorbent pants disposed within the housing portion, each pant defining a waist opening, two leg openings, a waist end, and a crotch end. At least a first pant and a second pant are positioned within the housing portion to be visible through the front transparent window, such that neither the waist end nor the crotch end of either the first pant or the second pant is visible through the front transparent window. In another embodiment, no elastically transversely gathered portions of either the first pant or the second pant are visible through the front transparent window. In another embodiment, first, second, and third pant folded heights are each approximately one-third of the height of a fourth pant.

22 Claims, 15 Drawing Sheets

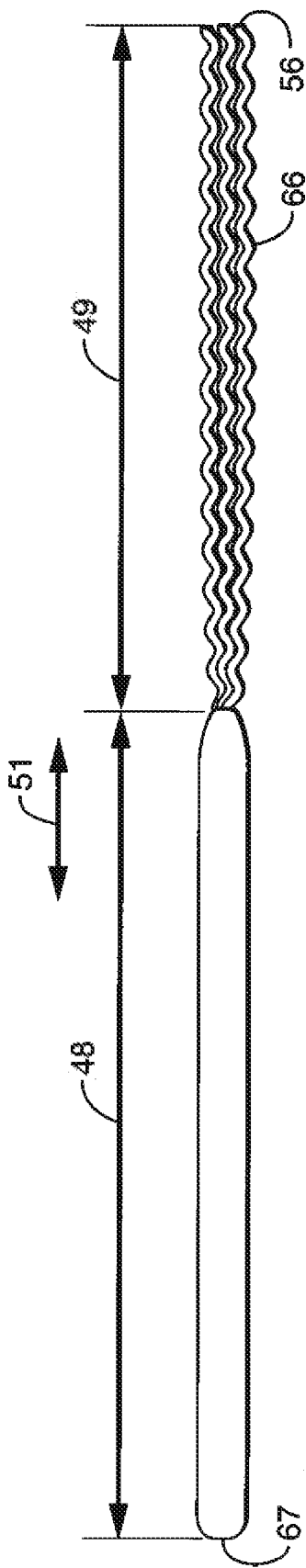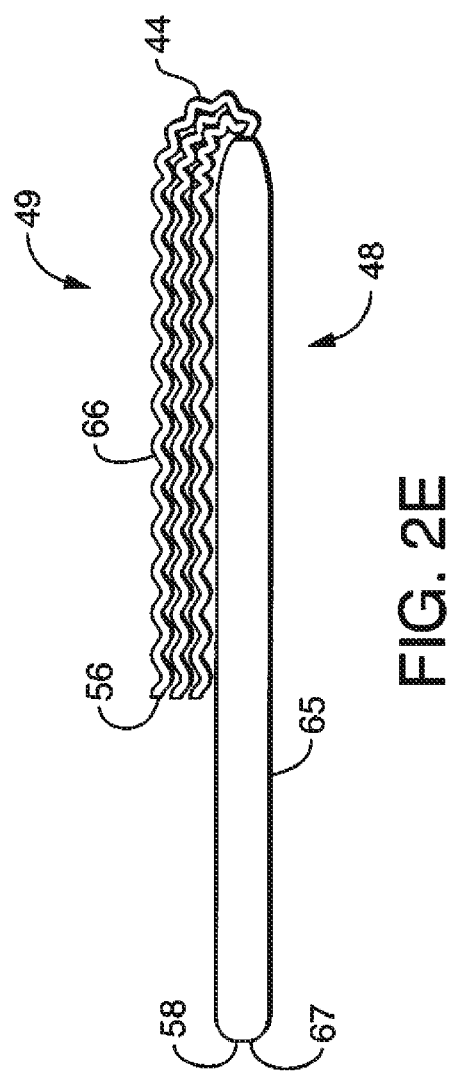
FIG. 2D
FIG. 2E

PACKAGE OF DISPOSABLE ABSORBENT PANTS

BACKGROUND

People rely on disposable absorbent garments in their everyday lives, including such garments as adult incontinence products, enuresis pants, training pants, and diapers. Many manufacturers seek to better meet the needs of users of such products. With certain products, such as adult incontinence underwear and enuresis pants, it is important that the garment feel as much as possible like "regular" underwear to promote an improved sense of normalcy to the wearer who suffers from incontinence or enuresis. Additionally, purchasers and users of such products are frequently embarrassed about their condition and about having to purchase products to deal with their incontinence or enuresis condition.

Currently, the most common method for obtaining incontinence and enuresis underwear is by purchasing relatively large bags in retail stores. Consumers are sometimes uncomfortable with having to place a large bag (e.g., 15 or more articles) of disposable absorbent garments in their cart, with having to proceed through checkout with this large bag, and/or with having this large bag present in their home. Furthermore, conventional packages of incontinence and enuresis underwear are opaque or mostly opaque, which some purchasers may perceive as overly "diaper-like" or too strongly connoting the presence of a personal care absorbent product directed to a urinary condition.

Therefore, there is a need for a package of incontinence or enuresis underwear that is smaller than conventional large bags of disposable absorbent underwear. There is also a need for a package of incontinence or enuresis underwear that better resembles "real underwear" so as to improve the feeling of normalcy for the purchaser/user.

U.S. 2004/0211696 published Oct. 28, 2004 in the name of Underhill et al. discloses a partially clear package of three rolled disposable training pants. However, the package disclosed in the '696 publication is not configured to provide optimal on-shelf upright stability, such as if the retailer or purchaser wished to stand the package upright on a shelf. In addition, it may be desirable to display disposable absorbent garments such that they appear relatively smooth and "cloth-like" through a package display window, minimizing the appearance of elastic gathers, which to some undesirably signify the presence of diaper-like personal care products. (Many conventional pant-like, pull-on style absorbent garments currently on the market, such as that depicted in FIG. 1, employ a product chassis in which multiple threads of elastic or sheets of elastic film are sandwiched between two nonwoven fabric layers, and such product are characterized by a large number of elastic gathers.) The package disclosed in the '696 publication does not provide a way to minimize or conceal such elastic gathers (such as, for example, waist elastic gathers), nor provide a way to conceal one or more ends or edges of the garments.

SUMMARY OF THE INVENTION

To better meet the above-described unmet needs in the art, a new package of disposable absorbent pants has been invented. In one embodiment, the package comprises a housing portion which defines a height and comprises a front panel extending in a front panel plane and a back panel extending in a back panel plane, the front panel plane being substantially parallel to the back panel plane, the front panel comprising a front transparent window. The package further includes a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion. At least a first pant and a second pant of the plurality of disposable absorbent pants are positioned within the housing portion to be visible through the front transparent window, such that neither the waist end nor the crotch end of either the first pant or the second pant is visible through the front transparent window.

In another embodiment, the package comprises a housing portion which defines a height and comprises a front panel extending in a front panel plane and a back panel extending in a back panel plane, the front panel plane being substantially parallel to the back panel plane, the front panel comprising a front transparent window. The package further includes a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, and each pant comprising elastically transversely gathered portions. At least a first pant and a second pant of the plurality of disposable absorbent pants are positioned within the housing portion to be visible through the front transparent window, such that no elastically transversely gathered portions of either the first pant or the second pant are visible through the front transparent window.

In still another embodiment, the package comprises a housing portion which defines a height and comprises a front panel extending in a front panel plane and a back panel extending in a back panel plane, the front panel plane being substantially parallel to the back panel plane, the front panel comprising a front transparent window. The package further includes a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, and each pant comprising elastically transversely gathered portions. Each of the plurality of pants is folded twice in the transverse direction such that the first and second side portions of each pant are folded over the respective center portion. At least a first pant, a second pant, and a third pant of the plurality of disposable absorbent pants are stacked within and along the height of the housing portion so as to be visible through the front transparent window, each of the first, second, and third pants being folded in the longitudinal direction such that the first, second, and third pants respectively define first, second, and third pant folded heights. The package further comprises a fourth pant, the fourth pant defining a fourth height which extends along the height of the housing portion. The first, second, and third pant folded heights are each approximately one-third of the fourth height.

In yet another embodiment, the package comprises a housing portion and a hanger portion positioned outside of the housing portion, the housing portion defining a height and comprising a front panel extending in a front panel plane and a back panel extending in a back panel plane, the front panel plane being substantially parallel to the back panel plane, the front panel comprising a front transparent window and the back panel comprising a back transparent window. The package further includes a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, and each pant comprising elastically transversely gathered portions. Each of the plurality of pants is folded twice in the transverse direction such that the first and second side portions of each pant are folded over the respective center portion. At least a first pant, a second pant, and a third pant of the plurality of disposable absorbent pants are stacked within and along the height of the housing portion so as to be visible through the front transparent window, each of the first, second, and third pants being folded three times in the longitudinal direction such that the first, second, and third pants respectively define first, second, and third pant folded heights. The package further comprises a fourth pant, a fifth pant, and a sixth pant, each of the fourth, fifth, and sixth pants being folded one time in the longitudinal direction such that the fourth, fifth, and sixth pants respectively define fourth, fifth, and sixth pant folded heights. The first, second, and third pant folded heights are each approximately one-third of the fourth pant folded height, are each approximately one-third of the fifth pant folded height, and are each approximately one-third of the sixth pant folded height. The first, second, and third pants are positioned within the housing portion to be visible through the front transparent window, such that neither the waist end nor the crotch end of any of the first, second, and third pants is visible through the front transparent window. The fourth pant is positioned within the housing portion to be visible through the back transparent window.

BRIEF DESCRIPTION OF THE DRAWINGS

FIG. 2D is a cross-sectional view of the pant of FIG. 2C as viewed along line 2D-2D.

FIG. 2E is similar to the view of FIG. 2D, but includes one longitudinal fold.

DEFINITIONS

Figure 1:
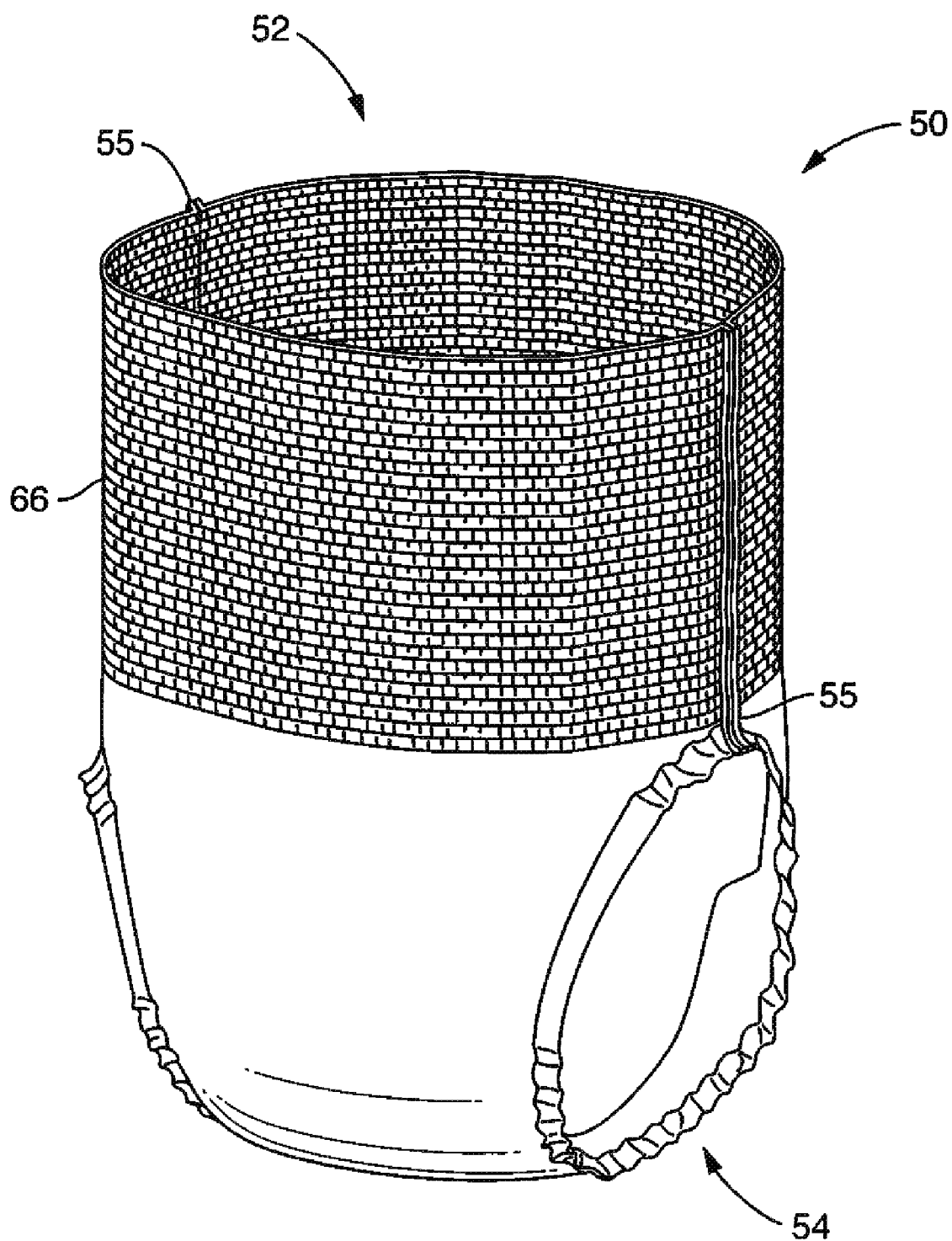
FIG. 1 representatively illustrates a perspective view of one example of a disposable absorbent pant suitable for use in conjunction with the present invention.

Within the context of this specification, each term or phrase below will include the following meaning or meanings. Additional terms are defined elsewhere in the specification.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Longitudinal" and "transverse" have their customary meaning, as indicated by the longitudinal and transverse axes depicted in the Figures. The longitudinal axis lies in the plane of the article and is generally parallel to a vertical plane that bisects a standing wearer into left and right body halves when the article is worn. The transverse axis lies in the plane of the article generally perpendicular to the longitudinal axis.

These terms may be defined with additional language in the remaining portions of the specification.

DETAILED DESCRIPTION OF EXEMPLARY EMBODIMENTS

Reference to the Figures shall be made in describing various aspects and embodiments of the invention. It should be noted that the embodiments depicted in the Figures and described herein are merely representative examples of the package of the invention. The various aspects and embodiments of the present invention are suitable for use with adult incontinence pants, prefastened disposable diapers, disposable swim pants, disposable training pants, disposable enuresis garments, and the like.

Referring to the FIGS. 3-4, the invention relates to a package 10 of disposable absorbent pants 50. The package includes a housing portion 12. The housing portion 12 houses or contains the pants 50 by partially or completely enclosing the pants 50. The housing portion 10 of the package may be formed by any suitable packaging material, such as, for example, plastic film, paperboard, or corrugated board. In one embodiment, the housing portion may comprise a plastic bag, such as a clear plastic bag. The housing portion may optionally include one or more inserts disposed within the package 10, such as a paperboard insert 14. In particular embodiments, indicia 40 may be disposed on or in the housing portion 12. The indicia 40 can communicate to the purchaser/user pertinent information about the garments, such as brand, count, size, absorbency, gender, and the like. The indicia 40 can be disposed on any portion or portions of the housing portion 12, such as on an outer surface 15 of the housing portion, or on a surface of the paperboard insert 14, as representatively illustrated in FIGS. 4A-4D.

The housing portion 12 defines a height 16, a width 17, and a depth 18. The housing portion 12 further comprises a front panel 20 and a back panel 30. The front panel 20 extends substantially within a front panel plane 21, and the back panel 30 extends substantially within a back panel plane 31. The front panel plane 21 is substantially parallel to the back panel plane 31. Note that it is not necessary for the front panel 20 and/or the back panel 30 to be perfectly planar or entirely flat; deviations from a perfectly flat plane are contemplated, particularly if the housing portion is constructed of flexible material and/or the pants 20 are packaged in a compressed manner such that they exert outward bulging forces on the housing portion 12. Rather, the intent is to communicate that in particular embodiments, the front panel 20 and the back panel are disposed in a reasonably parallel relationship to each other as shown in FIGS. 3-4. In particular embodiments, the housing portion 12 also includes a first side panel 23 and a second side panel 24 which together interconnect the front panel 20 to the back panel 30. The housing portion 12 may also include a top panel 25 and a bottom panel 26.

The package 10 may also include a hanger portion 13 disposed on the housing portion 12. One purpose of the hanger portion is to allow the package 10 to be hung from a hook or rod, such as in a retail store. For example, a hanger portion 13 may extend from the front panel 20, the back panel 30, and/or the top panel 25. In one embodiment, such as that representatively illustrated in FIGS. 3-4, the hanger portion 13 is formed of a flange 13a of material that extends from and is integral with one or more of the panels of the housing portion 12. Desirably, the hanger portion includes a hole 19 to allow the package 10 to be placed on a hook or rod.

The front panel 20 includes a front transparent window 22. The front transparent window 22 allows a purchaser/user to view, at least in part, the contents of the package 10 before the package is opened. The front transparent window 22 may extend over the entire area of the front panel 20, or over only a portion of the area of the front panel 20. For example, in the embodiment representatively illustrated in FIG. 4A in which the housing portion 12 comprises a clear plastic bag 42, an insert 14 covers a section of the front panel 20, and the front transparent window 22 visually surrounds the insert 14 on three sides. In another embodiment, indicia may be printed on a portion of the plastic bag 42 on the front panel 22, which, like the insert 14, would partially visually obscure the contents of the package 10.

In particular embodiments, the back panel 30 includes a back transparent window 32. The back transparent window 32 allows a purchaser/user to view, at least in part, the contents of the package 10 before the package is opened. The back transparent window 32 may extend over the entire area of the back panel 30, or over only a portion of the area of the back panel 30. For example, in the embodiment representatively illustrated in FIG. 4B in which the housing portion 12 comprises a clear plastic bag 42, an insert 14 covers a section of the back panel 30, and the back transparent window 32 visually surrounds the insert 14 on three sides. In another embodiment, indicia may be printed on a portion of the plastic bag 42 on the back panel 32, which, like the insert 14, would partially visually obscure the contents of the package 10.

In particular embodiments, the first side panel 23 and/or the second side panel 24 may also include transparent windows to allow a purchaser/user to at least partially view the contents of the package 10 before the package is opened 10. Alternatively, the first side panel 23 and/or the back side panel 24 may be partially or entirely obscured by printed indicia and/or an opaque insert. For example, in one desirable embodiment representatively illustrated in FIGS. 4A-4D, the housing portion 12 includes a U-shaped opaque, paperboard insert 14 which partially obscures the front panel 20, the first side panel 23, and the back panel 30, partially defining the front transparent window 22, two small first side transparent windows 33a and 33b, and the back transparent window 32. In the embodiment of FIG. 4, a second side transparent window 34, a top transparent window 35, and a bottom transparent window 36 are each substantially unobscured and allow ready visibility into the contents of the package 10.

The package 10 further includes a plurality of disposable absorbent pants disposed within the housing portion 12. Each pant 50 defines a waist opening 52, two leg openings 54, a waist end 56, and a crotch end 58. In particular embodiments, each pant includes two side seams 55. Each pant defines a longitudinal direction 51 that extends from the waist end 56 to the crotch end 58, and each pant defines a transverse direction 53 that is perpendicular to the longitudinal direction 51. Each pant defines a length 57 which extends in the longitudinal direction 51 and a width 59 which extends in the transverse direction 53. The length 57 and width 59 for purposes herein are measured when the pant is in a fully assembled (side seams intact), relaxed condition, such as that depicted in FIG. 2A. Each pant further defines a first side portion 60, a second side portion 62, and a center portion 64 positioned transversely between the first side portion 60 and the second side portion 62. The first side portion 60 extends 20% to 40% of the transverse width 59 of the pant 50 in a laid-flat, relaxed condition. The second side portion 62 extends 20% to 40% of the transverse width 59 of the pant 50 in a laid-flat, relaxed condition. The center portion 64 extends approximately 20% to 50% of the width 59 of the pant 50 in a laid-flat, relaxed condition. In particular embodiments, the first side portion 60, the second side portion 62, and the center portion 64 each extend approximately one-third of the width 59 of the pant 50 in a laid-flat, relaxed condition, as is generally representatively illustrated in FIG. 2A.

Each pant also desirably includes an absorbent composite 65 generally disposed in the center portion in a crotch region 68, and extending longitudinally from the crotch end 58 toward the waist end 56. In particular embodiments, the absorbent composite 65 can but need not include a liquid-impermeable backsheet, a liquid-permeable topsheet, and a fluid-absorbing core comprised of fluff pulp and/or superabsorbent polymer. In the example representatively illustrated in FIG. 2, the absorbent composite 65 extends approximately one-half of the length 57 of the pant 50. In the FIGS. 2D-2G, 3E, and 3F, the crotch region 48 of each pant 50 that includes the absorbent composite 65 is shown as being thicker than the waist region 49 of the pant (which does not include the absorbent composite 65).

In particular embodiments, each pant 50 includes elastically transversely gathered portions 66. For example, certain disposable absorbent underwear pants employ a product chassis in which one or more elastic members are sandwiched between two nonwoven fabric layers. The elastic members may impart a gathering force primarily in the transverse direction 53. In this way, when the pant is worn, the elastic members extend around the body, such that the elastic or gathering forces extend primarily around the wearer's waist. In one example, an hourglass-shaped panel comprising an elastomeric film laminate is employed. In particular embodiments, the laminate comprises two nonwoven layers superposed on opposing top and bottom surfaces of an elastomeric polymeric film such that the elastomeric polymeric film is sandwiched between the two nonwoven facings. In another example, an hourglass panel is provided which comprises a nonwoven substrate which is imparted with elastic properties by adhesively attaching elastic strands thereto. The strands and adhesive can be sandwiched to the hourglass panel with a second nonwoven layer or layers. In certain variations on the above embodiments, separate, spaced-apart front and back panels—each of which exhibits elastomeric transverse gathering—are interconnected by an absorbent composite. Examples of disposable underwear having elastically transversely gathered portions are disclosed in U.S. Pat. No. 5,745,922 issued May 5, 1998 to Rajala et al., in U.S. Pat. No. 6,240,569 issued Jun. 5, 2001 to Van Gompel et al., and in U.S. Pat. No. 6,702,798 issued Mar. 9, 2004 to Christoffel et al. As used herein, "elastically transversely gathered" means gathered by at least 20% from a fully elongated, taut condition. For example, if the waist band region of a pant measures 50 centimeters in transverse length when fully elongated in the transverse direction, the waistband region is considered elastically transversely gathered if, upon removal of the elongating force, the waistband region transversely contracts to 40 centimeters or less.

Figure 2A:
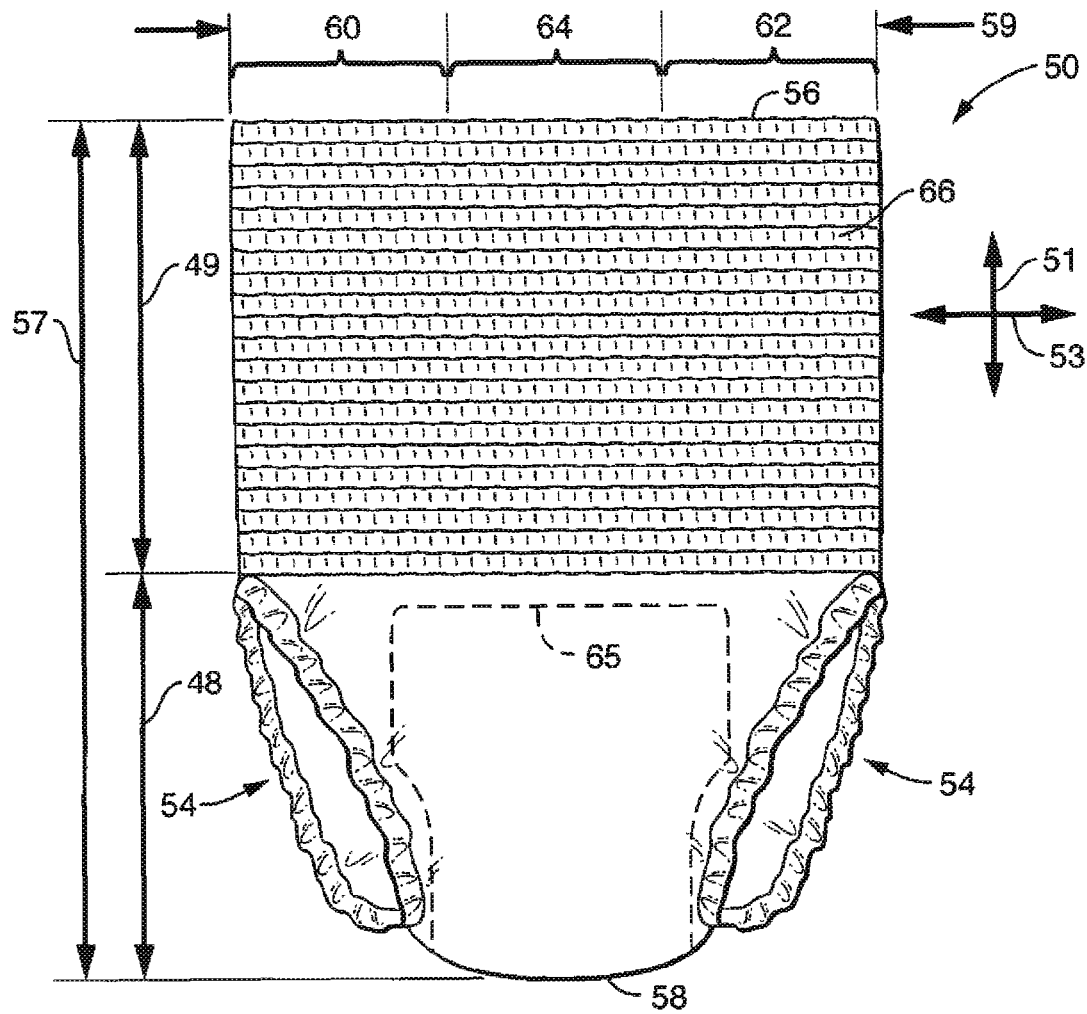
FIG. 2A representatively illustrates a front plan view of the disposable absorbent pant of FIG. 1, shown in a relaxed and laid-flat condition.
Figure 2B:
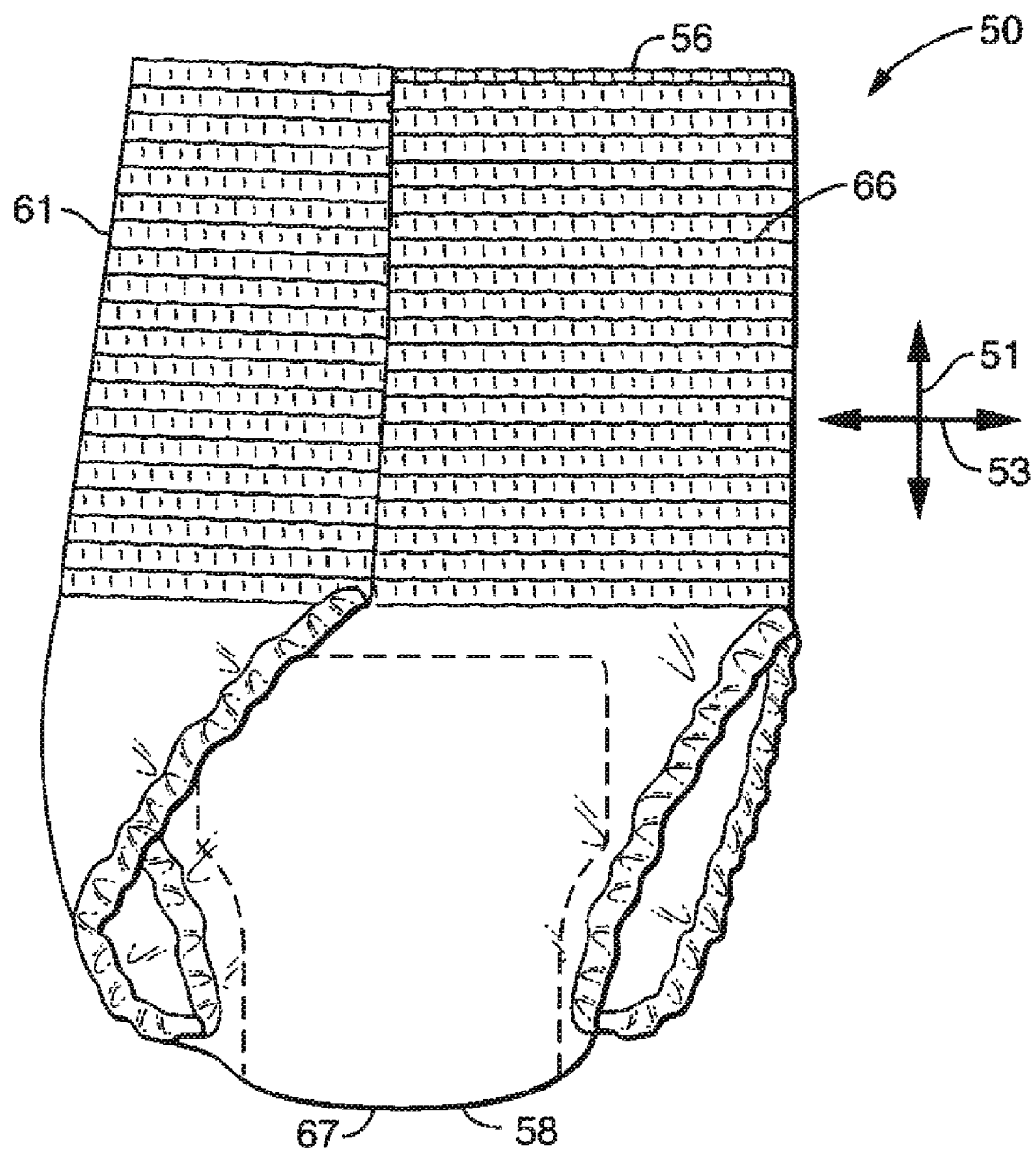
FIG. 2B representatively illustrates a front plan view of the disposable absorbent pant of FIG. 2A, shown in a relaxed and laid-flat condition, with one side portion folded over the center portion.
Figure 2C:
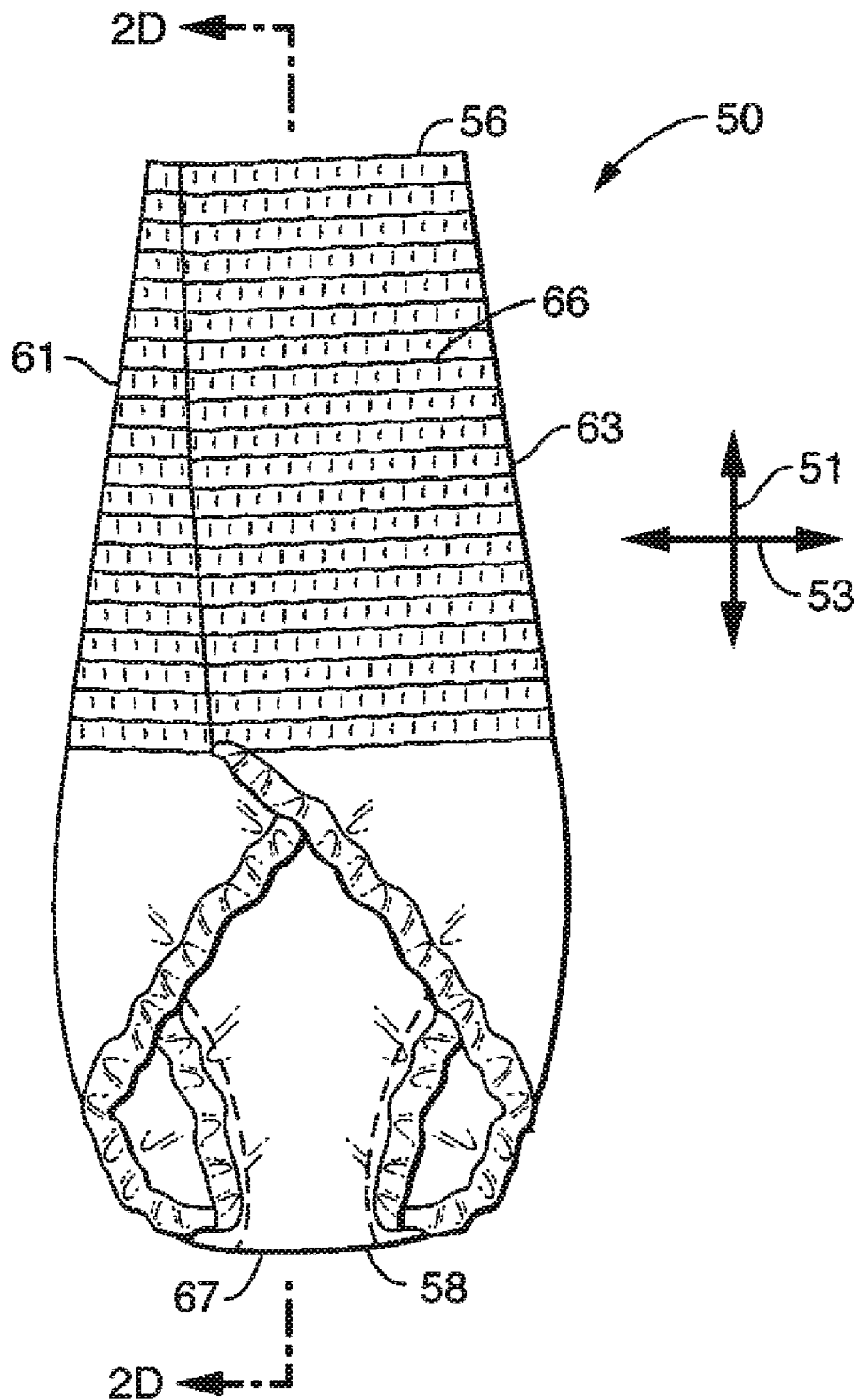
FIG. 2C representatively illustrates a front plan view of the disposable absorbent pant of FIG. 2A, shown in a relaxed and laid-flat condition, with both side portions folded over the center portion.

In particular embodiments, one, more than one, or, most preferably, all of the plurality of pants 50 is/are folded twice in the transverse direction 53. In particular embodiments, as representatively illustrated in FIGS. 2A-2C, the first side portion 60 and the second side portion 62 of each pant 50 are folded over the center portion 64. In FIG. 2A, the pant 50 is shown in a relaxed, unfolded condition. In FIG. 2B, the first side portion 60 is shown folded over the center portion 64 at first transverse fold line 61. In FIG. 2C, the second side portion 62 is shown folded over both the center portion 64 and the first side portion 60 at second transverse fold line 63. In this way, the pant 50 is folded twice in the transverse direction 53. In alternative embodiments, the first side portion 60 and the second side portion 62 can both be tucked within—as opposed to folded over—the center portion 64 (not shown). Representative examples of disposable pants having side portions tucked into a center portion and methods to so tuck are disclosed in U.S. Pat. No. 6,723,035 issued Apr. 20, 2004 to Franklin et al., and the entirety of the portions of the '035 patent that relate to tucked side portions or tucked panels is hereby incorporated by reference to the extent consistent herewith.

In particular embodiments, one, more than one, or all of the plurality of pants 50 is/are folded at least once in the longitudinal direction 51. In particular embodiments, as representatively illustrated in FIG. 2E, the pant 50 is folded at first longitudinal fold line 44 such that the waist end 56 lies atop the absorbent composite 65. As representatively illustrated in FIG. 2E, the first longitudinal fold line 44 can be, but need not be, longitudinally near the end of the absorbent composite 65. Note that for the purposes of the present disclosure, the crotch fold 67 of the pant 50 is ignored for purposes of counting the number of times that the pant is folded in the longitudinal direction 51. For example, for purposes of the present disclosure, the pant 50 depicted in FIG. 2E is considered to be folded twice in the transverse direction 53 (namely, at transverse fold lines 61 and 63), but just once in the longitudinal direction 51 (namely, at first longitudinal fold line 44). Similarly, for purposes of the present disclosure, the pant configuration depicted in FIG. 2D is considered to be folded twice in the transverse direction 53 (namely, at transverse fold lines 61 and 63), but as having no folds in the longitudinal direction 51.

In particular embodiments, as representatively illustrated in FIGS. 3 and 4, at least a first pant 70 and a second pant 80 of the plurality of disposable absorbent pants are positioned within the housing portion 12 to be visible through the front transparent window 22, such that neither the waist end 56 nor the crotch end 58 of either the first pant 70 or the second pant 80 is visible through the front transparent window 22. In other words, while at least some portion of the first pant 70 and of the second pant 80 is visible through the front transparent window 22, neither the waist end 56 nor the crotch end 58 of either pant 70, 80 is visible through the front transparent window 22. In this way, the purchaser/user can see the first and second pants 70, 80 inside the package, but the pants 70, 80 are presented in a neat and tidy manner. In particular embodiments, such as those depicted in FIGS. 3 and 4, the package further includes a third pant 90 positioned within the housing portion 12 such that neither the waist end 56 nor the crotch end 58 of the third pant 90 is visible through the front transparent window 22.

In particular embodiments, as representatively illustrated, in FIGS. 3 and 4, at least a first pant 70 and a second pant 80 of the plurality of disposable absorbent pants are positioned within the housing portion 12 to be visible through the front transparent window 22, such that no elastically transversely gathered portions 66 of either the first pant 70 or the second pant 80 are visible through the front transparent window 22. In other words, while at least some portion of the first pant 70 and of the second pant 80 is visible through the front transparent window 22, no elastically transversely gathered portions 66 of either pant 70, 80 is visible through the front transparent window 22. In this way, the purchaser/user can see the first and second pants 70, 80 inside the package, but the pants 70, 80 are presented in a neat and tidy manner. In particular embodiments, such as those depicted in FIGS. 3 and 4, the package further includes a third pant 90 positioned within the housing portion 12 such that no elastically transversely gathered portions 66 of the third pant 90 are visible through the front transparent window 22.

Figure 2F:
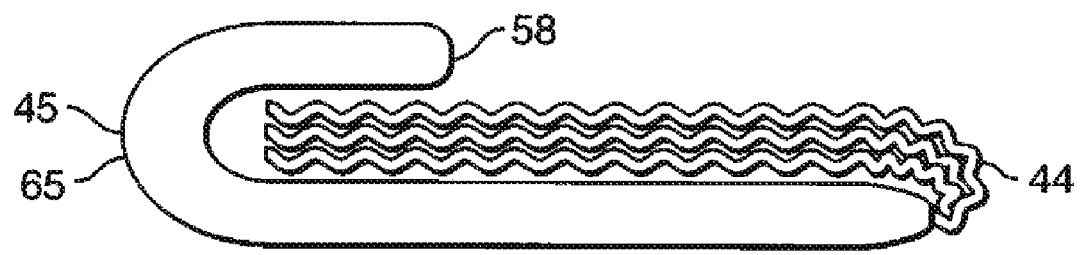
FIG. 2F is similar to the view of FIG. 2D, but includes two longitudinal folds.
Figure 2G:
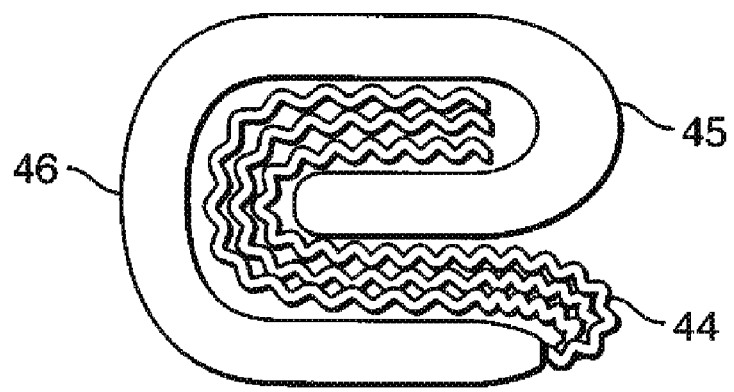
FIG. 2G is similar to the view of FIG. 2D, but includes three longitudinal folds.
Figure 3A:
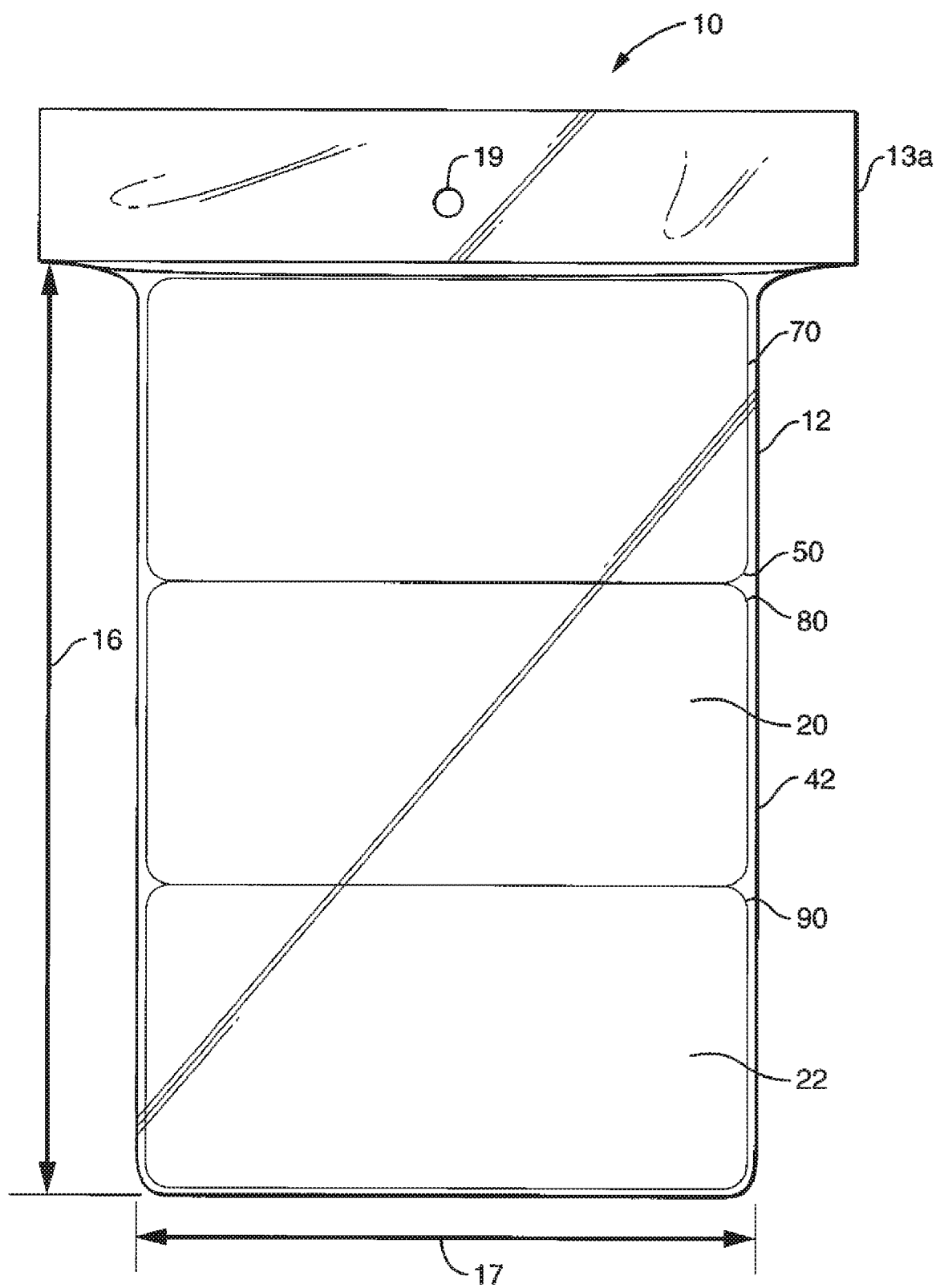
FIG. 3A representatively illustrates a front view of one embodiment of the package of the present invention.
Figure 3B:
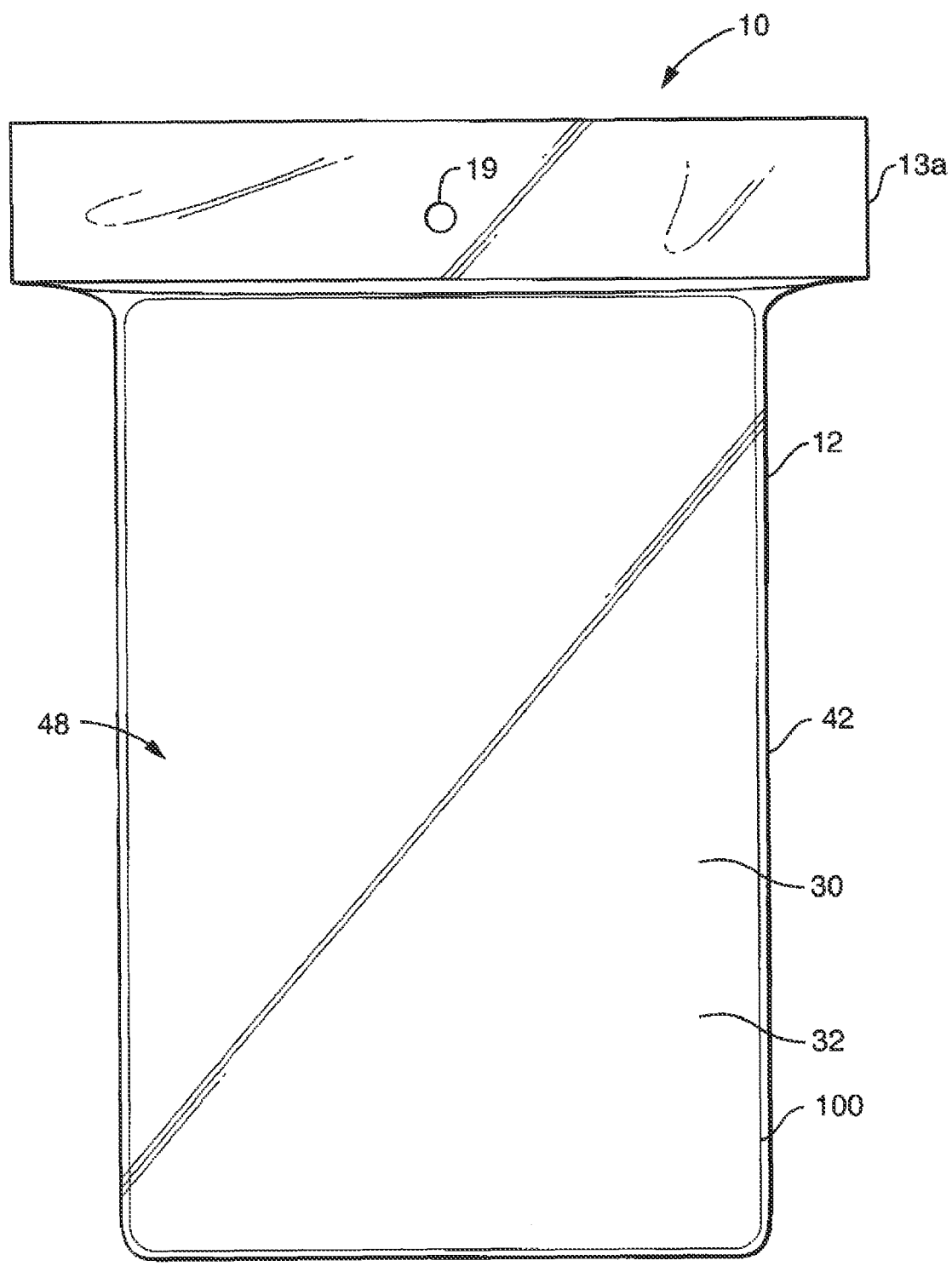
FIG. 3B representatively illustrates a back view of the embodiment of FIG. 3A.
Figure 3C:
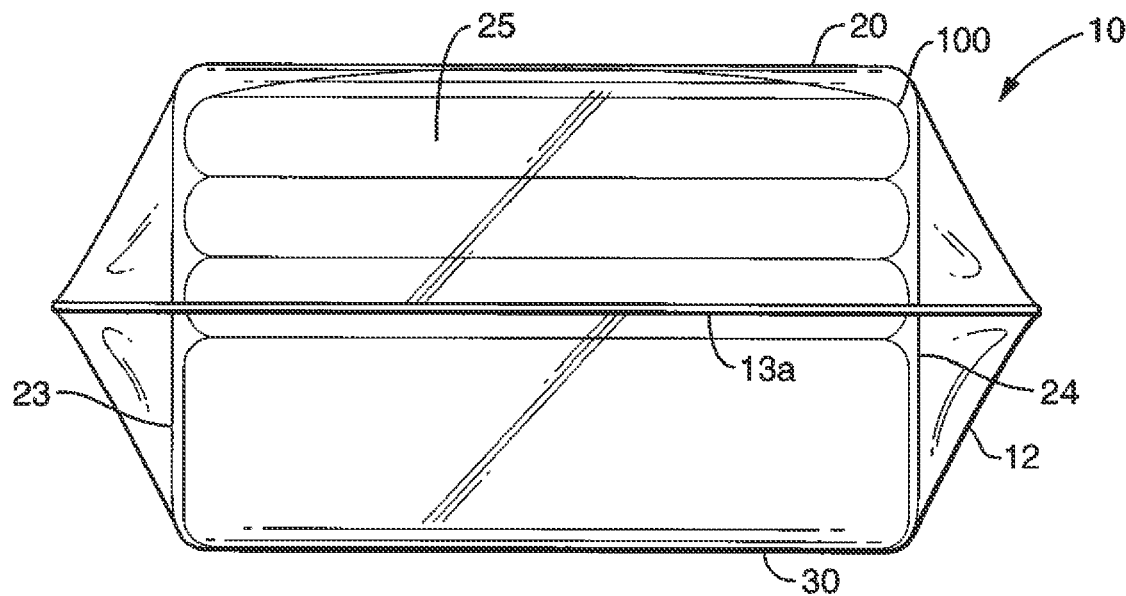
FIG. 3C representatively illustrates a top view of the embodiment of FIG. 3A.
Figure 3D:
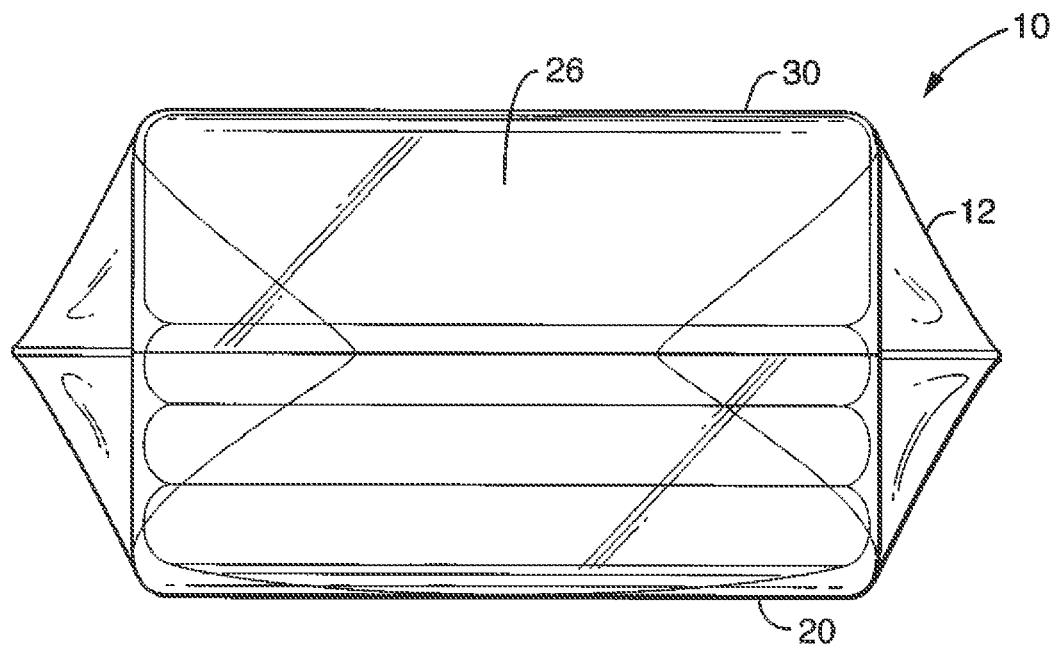
FIG. 3D representatively illustrates a bottom view of the embodiment of FIG. 3A.
Figure 3E:
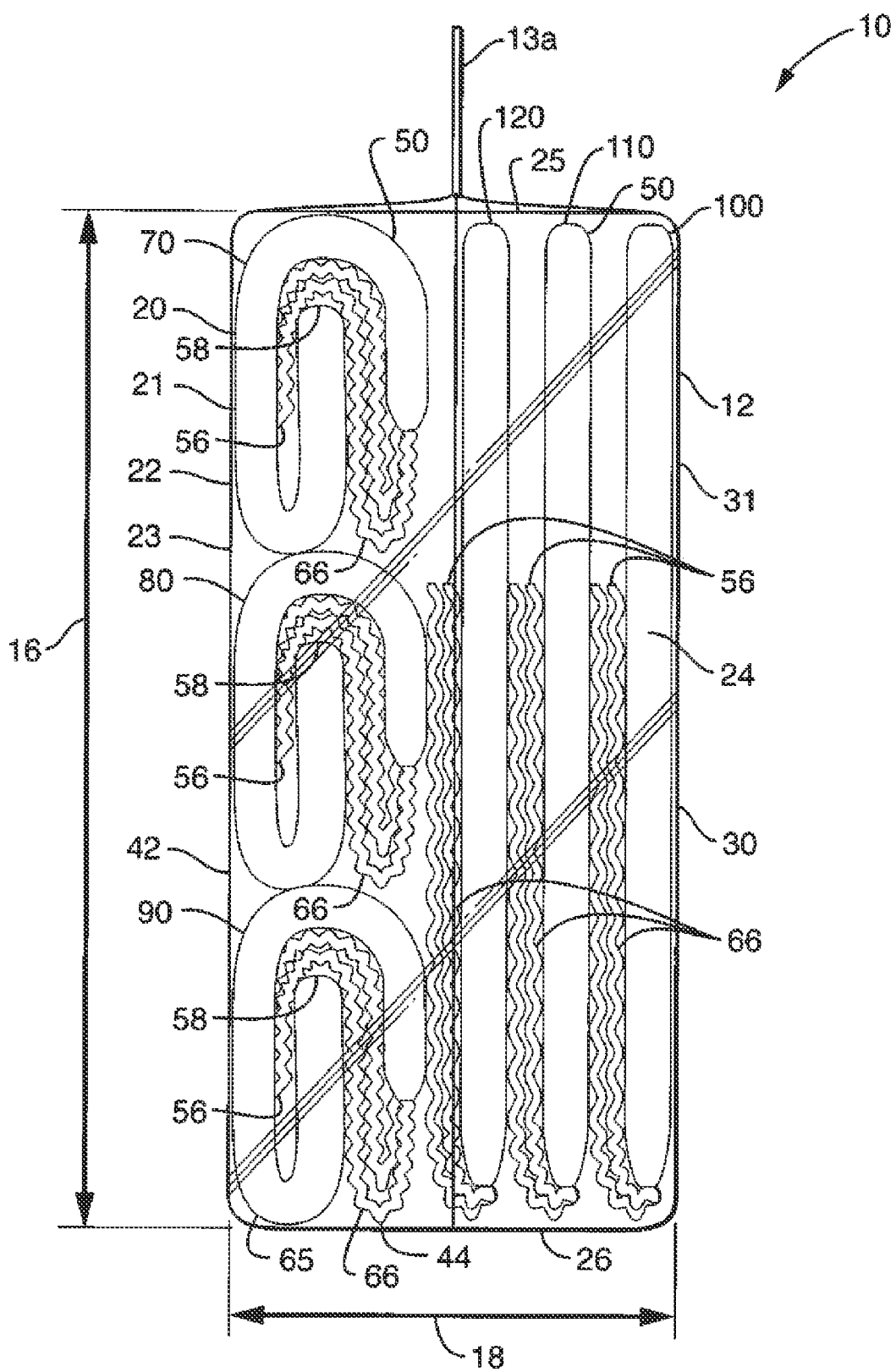
FIG. 3E representatively illustrates a first side view of the embodiment of FIG. 3A.
Figure 3F:
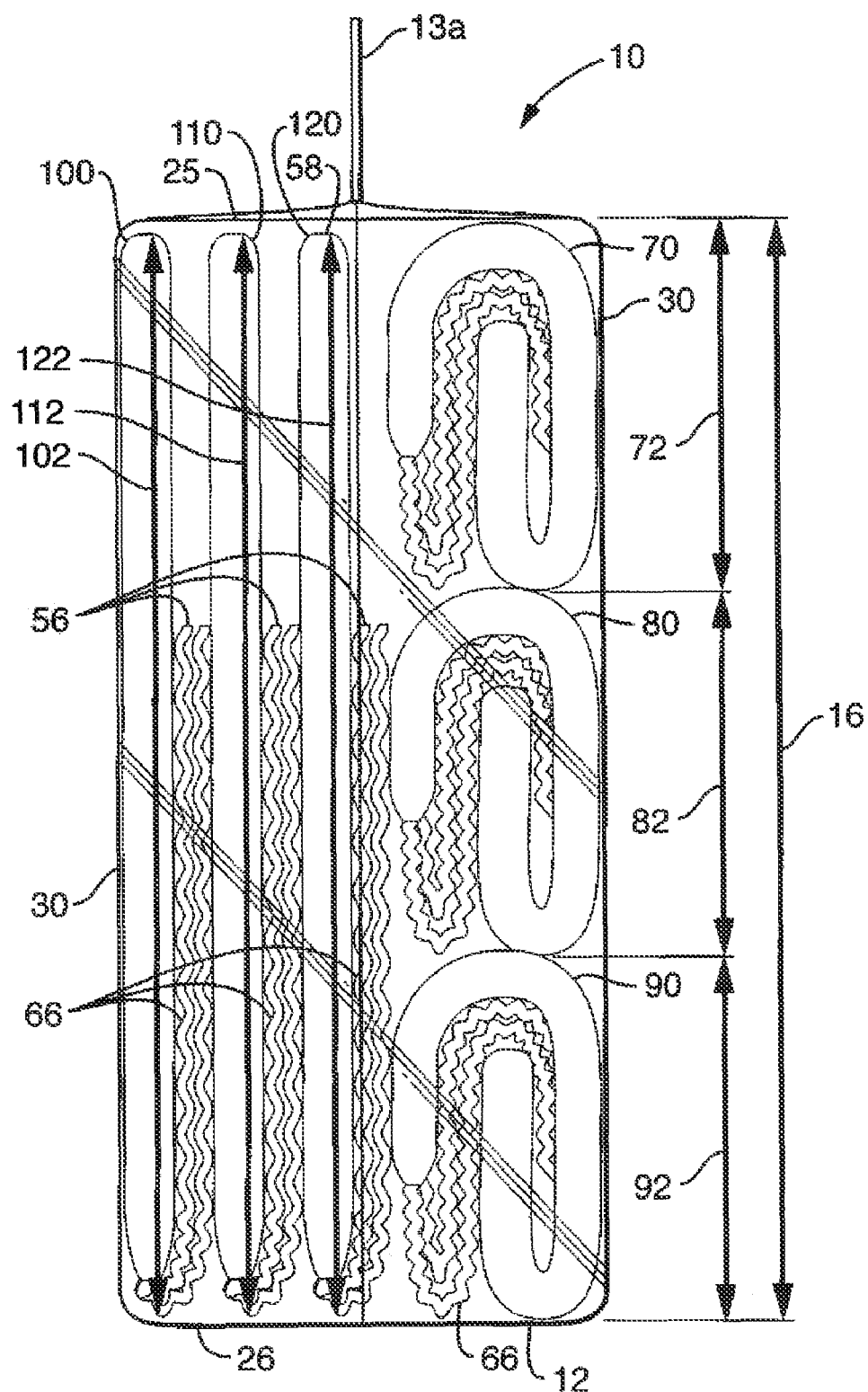
FIG. 3F representatively illustrates a second side view of the embodiment of FIG. 3A.
Figure 4A:
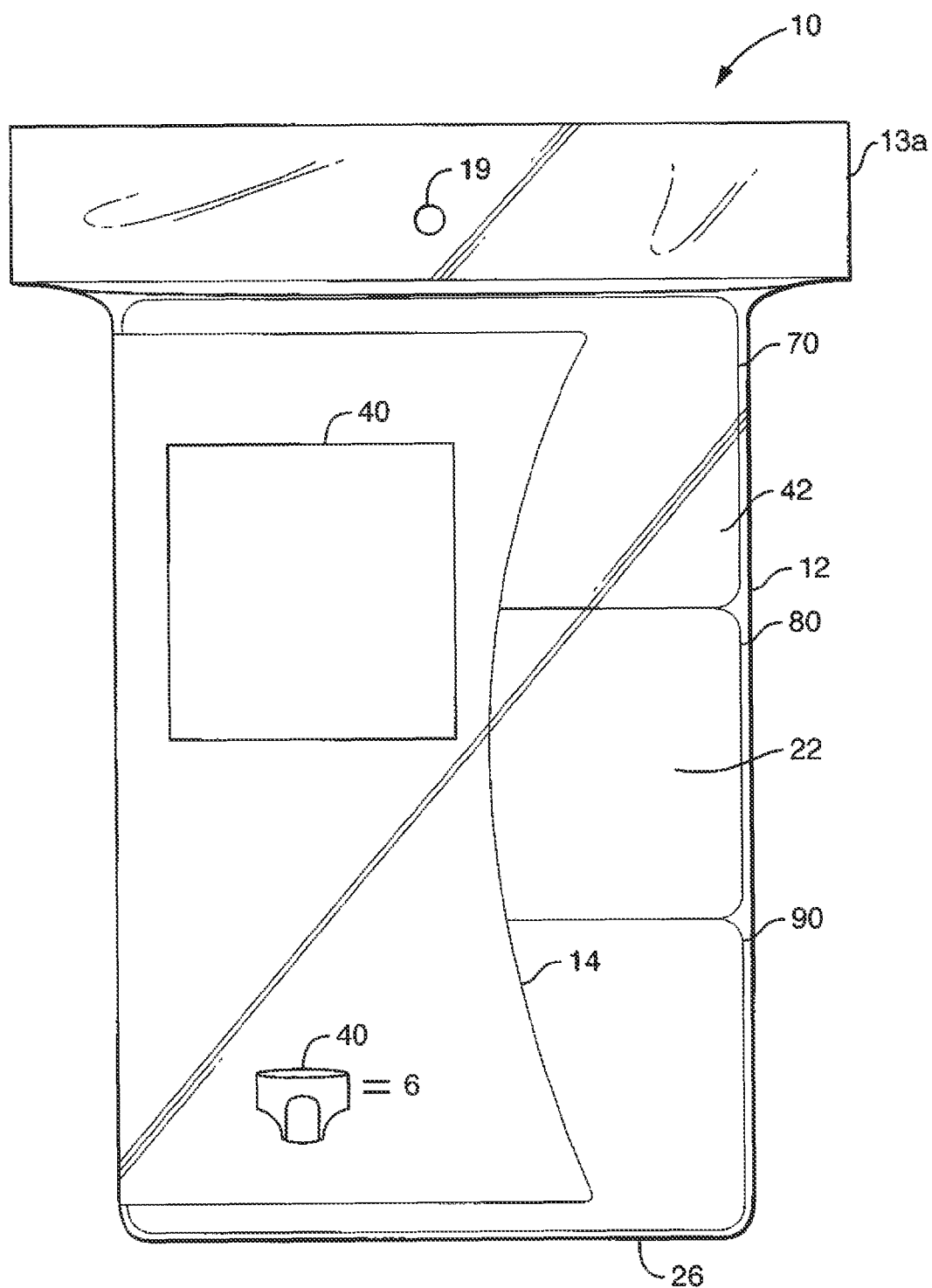
FIG. 4A representatively illustrates a front view of an alternative embodiment of the package of the present invention.
Figure 4B:
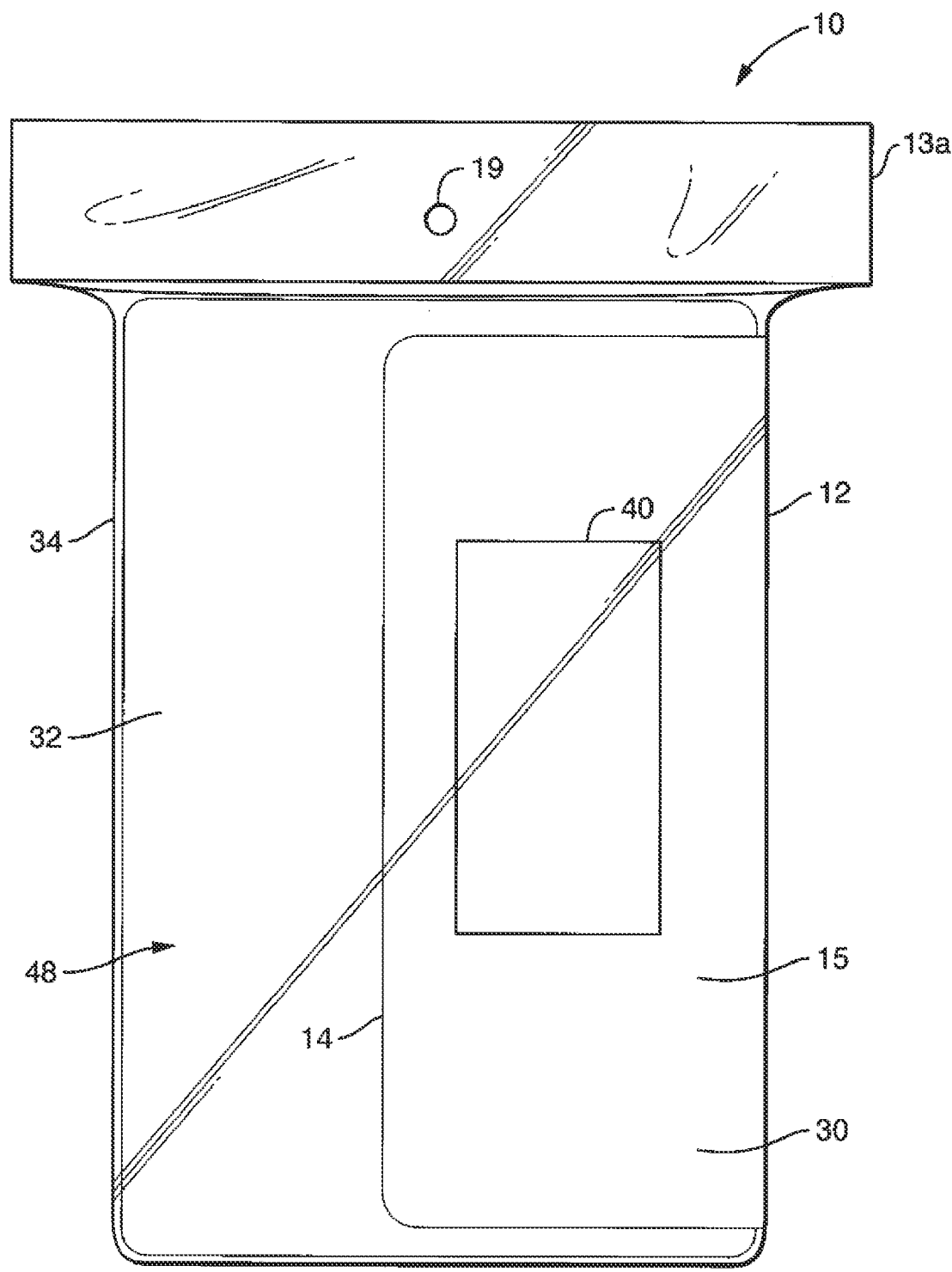
FIG. 4B representatively illustrates a back view of the embodiment of FIG. 4A.
Figure 4C:
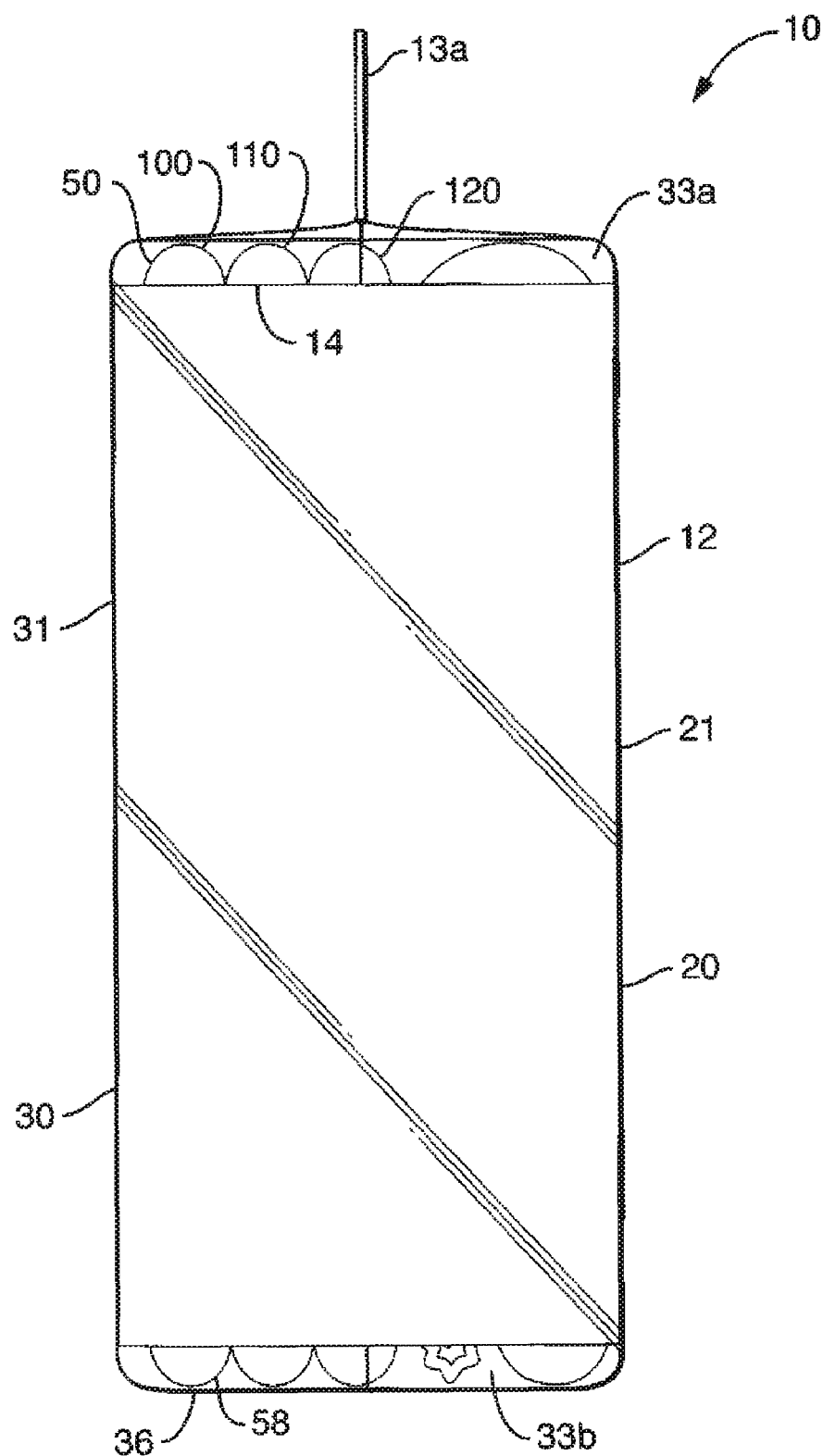
FIG. 4C representatively illustrates a first side view of the embodiment of FIG. 4A.
Figure 4D:
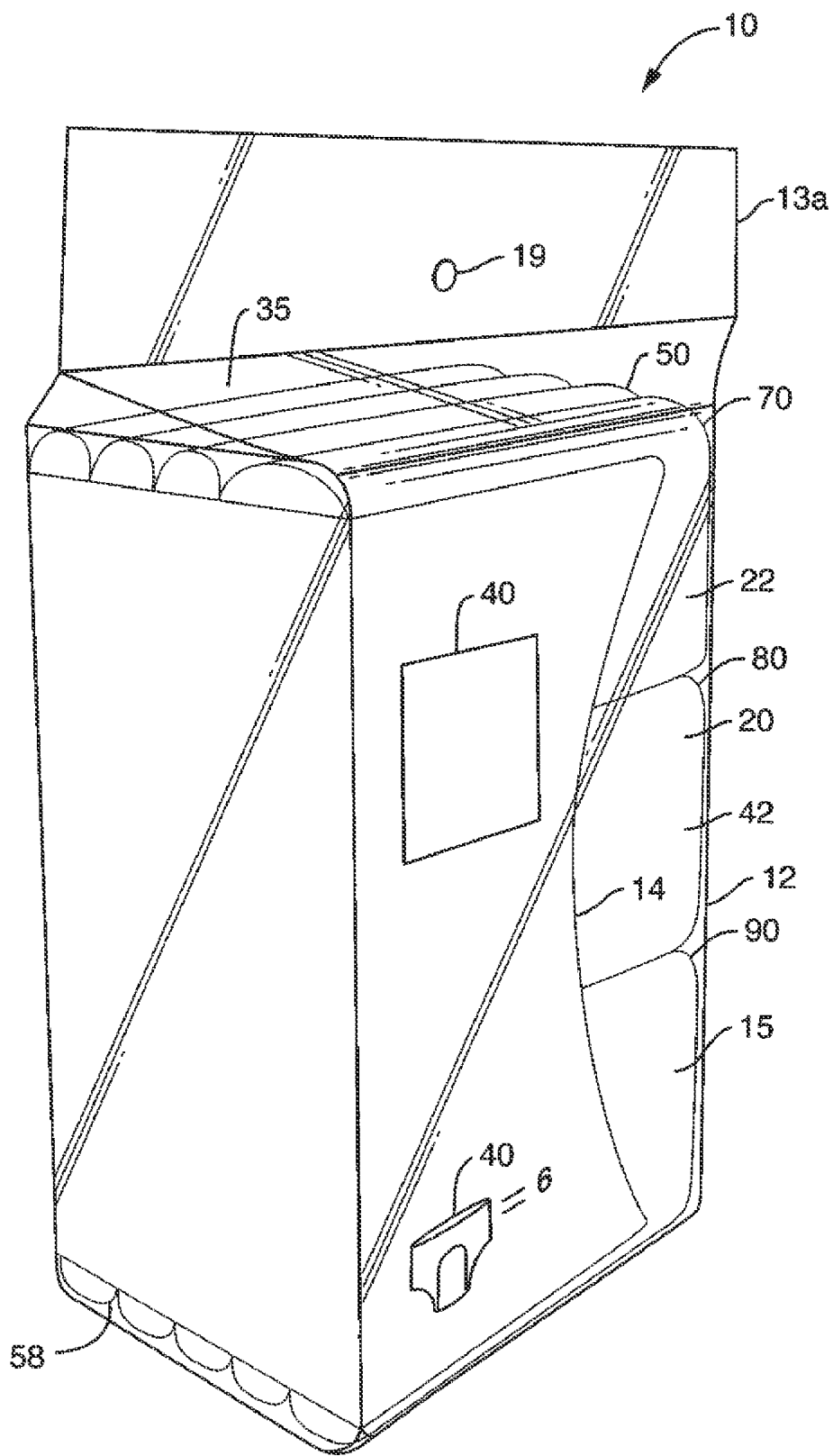
FIG. 4D representatively illustrates a perspective view of the embodiment depicted by FIGS. 4A-4C.

In one preferred embodiment, the first and second pants 70, 80 (or, alternatively, the first, second, and third pants 70, 80, 90) are each folded twice in the longitudinal direction 51. For example, in particular embodiments, as representatively illustrated in FIG. 2F, the pant 50, after being folded at the first longitudinal fold line 44 as shown in FIG. 2E, is further folded at a second longitudinal fold line 45. In a particularly preferred embodiment, the first and second pants 70, 80 (or, alternatively, the first, second, and third pants 70, 80, 90) are each folded three times in the longitudinal direction 51. For example, as representatively illustrated in FIG. 2G, the pant 50, after being folded at the first and second longitudinal fold lines 44, 45 as shown in FIGS. 2E and 2F, is further folded at a third longitudinal fold line 46. Following this repeated folding in the longitudinal direction 51, the pant 50 assumes a somewhat "rolled" appearance. In particular embodiments, the folded pant configuration depicted in FIG. 2G is an effective way of concealing the waist end 56 and the crotch end 58, which is advantageous for the reasons described earlier. In particular embodiments, one or more of the first, second, and/or third pants 70, 80, 90 can be folded four times in the longitudinal direction 51. In one particularly desirable embodiment, visible in FIGS. 3E and 3F, the bottom pant (i.e., the third pant 90 in FIGS. 3E and 3F) is positioned within the housing portion 12 so that the first longitudinal fold line 44 and the second longitudinal fold line 45 faces the bottom panel. This configuration provides excellent package integrity and "stand-up" stability.

As representatively illustrated in FIGS. 3-4, the package 10 can further comprise an additional pant, such as a fourth pant 100, which extends substantially the entire height 16 (i.e., at least 80% of the height) of the housing portion 12. In particular embodiments, the fourth pant 100 is positioned within the housing portion 12 to be visible through the back transparent window 32, but such that the waist end 56 of the fourth pant 100 is not visible through the back transparent window 32. For example, in the examples of FIGS. 3 and 4, a fourth pant 100, folded in the manner depicted in FIG. 2E, is positioned within the housing portion 12 such that its waist end 56 is concealed with the package, hidden from view through the back transparent window 32. In this way, the purchaser/user can see the fourth pant 100 inside the package, but the pant 100 is presented in a neat and tidy manner. In certain embodiments, the waist end 56 of the fourth pant 100 may also not be visible through one or both of the side transparent windows 33/34.

In particular embodiments, the fourth pant 100 is positioned within the housing portion 12 to be visible through the back transparent window 32, but such that no elastically transversely gathered portions 66 are visible through the back transparent window 32. For example, in the examples of FIGS. 3 and 4, a fourth pant 100, folded in the manner depicted in FIG. 2D, is positioned within the housing portion 12 such that its elastically transversely gathered portions 66 are concealed with the package, hidden from view. In this way, the purchaser/user can see the fourth pant 100 inside the package, but the pant 100 is presented in a neat and tidy manner. In a particular embodiment of the package 10, the crotch region 48 of each pant 50 comprises an absorbent composite 65 and is substantially free of elastically transversely gathered portions, and the waist region 49 of each pant 50 comprises elastically transversely gathered portions. The crotch region 48 of each of the first and second pants 70, 80 is visible through the front transparent window 22, and the crotch region 48 of the fourth pant 100 is visible through the back transparent window 32. Further, the waist region 49 of each of the first and second pants 70, 80 is not visible through the front transparent window 22, and/or the waist region 49 of the fourth pant 100 is not visible through the back transparent window 32.

In particular embodiments, the package 10 further comprises a fifth pant 110. The fifth pant 110, like the fourth pant 110, extends substantially the entire height 16 of the housing portion 12. The fifth pant 110 is positioned within the housing portion 12 such that the fifth pant 110 is neither visible through the front transparent window 22 nor visible through the back transparent window 32. This is because in the illustrated embodiment, the fifth panel 110 is sandwiched between the fourth pant 100 to its back and the stack of first, second, and third pants 70, 80, 90 to its front. In particular embodiments, the fourth pant 100 is visible through the first side transparent window 33, the second side transparent window 34, the top transparent window 35, and/or the bottom transparent window 36. In particular embodiments, the fifth pant 110 is visible through the first side transparent window 33, the second side transparent window 34, the top transparent window 35, and/or the bottom transparent window 36.

In particular embodiments of the package 10, such as those embodiments representatively illustrated in FIGS. 3 and 4, a first pant 70, a second pant 80, and a third pant 90 are stacked within and along the height 16 of the housing portion 12 so as to be visible through the front transparent window 22. In this embodiment, each of the first, second, and third pants 70, 80, 90 are folded in the longitudinal direction 51 such that the first pant 70 defines a first pant folded height 72, the second pant 80 defines a second pant folded height 82, and the third pant 90 defines a third pant folded height 92. The package 10 of this embodiment further includes a fourth pant 100 which defines a fourth height 102 that extends along the same direction as the height 16 of the housing portion 12. The fourth pant 100 in this embodiment may be folded one or more times, or not folded at all. In the example of FIG. 3, the fourth pant 100 is folded one time in the longitudinal direction 51 at the longitudinal fold line 44, and it is this folded configuration that in this embodiment defines the fourth height 102 of the fourth pant 100. The fourth height 102 may be equal to, or less than, the height 16 of the housing portion 12. The first pant folded height 72, the second pant folded height 82, and the third pant folded height 92 are each approximately one-third of the fourth height 102.

In one variant, the package 10 further includes a fifth pant 110 which defines a fifth height 112 that extends along the same direction as the height 16 of the housing portion 12. As with the fourth pant 100, the fifth pant 110 in this embodiment may be folded one or more times, or not folded at all. In the example of FIG. 3, the fifth pant 110 is folded one time in the longitudinal direction 51 at the longitudinal fold line 44, and it is this folded configuration that in this embodiment defines the fifth height 112 of the fifth pant 110. As with the fourth height 102, the fifth height 112 may be equal to, or less than, the height 16 of the housing portion 12. The first pant folded height 72, the second pant folded height 82, and the third pant folded height 92 are each approximately one-third of the fifth height 112. The fifth pant 110 may be positioned within the housing portion 12 such that the fifth pant 110 is neither visible through the front transparent window 22 nor visible through the back transparent window 32.

In particular embodiments, the package 10 of various embodiments of the present invention may also include additional pants, such as a sixth pant 120 defining a sixth height 122. The sixth pant 120 may exhibit any of the characteristics described above in conjunction with the fifth pant 110. In one example, the first pant folded height 72, the second pant folded height 82, and the third pant folded height are each approximately one-third of the sixth height 122. The sixth pant 120 may be positioned within the housing portion 12 such that the sixth pant 120 is neither visible through the front transparent window 22 nor visible through the back transparent window 32. In one desirable embodiment of the package 10, the first pant 70 and the fourth pant 100 exhibit a first color or first printed pattern, the second pant 80 and the fifth pant 110 exhibit a second color or second printed pattern, and the third pant 90 and the sixth pant 120 exhibit a third color or third printed pattern. The first color/first printed pattern is visually different from the second color/second printed pattern, the second color/second printed pattern is visually different from the third color/third printed pattern, and the third color/third printed pattern is visually different from the first color/first printed pattern. Such a configuration creates a garment-like "variety pack" of disposable absorbent underwear.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A package of disposable absorbent pants, the package comprising:
    a housing portion which defines a height and comprises a front panel extending in a front panel plane and a back panel extending in a back panel plane, the front panel plane being substantially parallel to the back panel plane, the front panel comprising a front transparent window;
    a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion;
    wherein at least a first pant and a second pant of the plurality of disposable absorbent pants are positioned within the housing portion to be visible through the front transparent window, such that neither the waist end nor the crotch end of either the first pant or the second pant is visible through the front transparent window; a third pant positioned within the housing portion such that neither the waist end nor the crotch end of the third pant is visible through the front transparent window; and
    wherein the back panel comprises a back transparent window, the package further comprising a fourth pant, the fourth pant extending substantially the entire height of the housing portion, the fourth pant positioned within the housing portion to be visible through the back transparent window, such that the waist end of the fourth pant is not visible through the back transparent window.

2. The package of claim 1, wherein each of the plurality of pants is folded twice in the transverse direction such that the first and second side portions of each pant are folded over the respective center portion.

3. The package of claim 1, wherein the first, second, and third pants are each folded twice in the longitudinal direction.

4. The package of claim 3, wherein the first, second, and third pants are each folded three times in the longitudinal direction.

5. The package of claim 1 further comprising a fifth pant, the fifth pant extending substantially the entire height of the housing portion, the fifth pant positioned within the housing portion such that the fifth pant is neither visible through the front transparent window nor visible through the back transparent window.

6. A package of disposable absorbent pants, the package comprising:
    a housing portion which defines a height and comprises a front panel extending in a front panel plane and a back panel extending in a back panel plane, the front panel plane being substantially parallel to the back panel plane, the front panel comprising a front transparent window;
    a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, and each pant comprising elastically transversely gathered portions;
    wherein at least a first pant and a second pant of the plurality of disposable absorbent pants are positioned within the housing portion to be visible through the front transparent window, such that no elastically transversely gathered portions of either the first pant or the second pant are visible through the front transparent window and a third pant positioned within the housing portion such that no elastically transversely gathered portions of the third pant are visible through the front transparent window; and
    wherein the back panel comprises a back transparent window, the package further comprising a fourth pant, the fourth pant extending substantially the entire height of the housing portion, the fourth pant positioned within the housing portion to be visible through the back transparent window, such that the waist end of the fourth pant is not visible through the back transparent window.

7. The package of claim 6 wherein each of the plurality of pants is folded twice in the transverse direction such that the first and second side portions of each pant are folded over the respective center portion.

8. The package of claim 6 wherein the first, second, and third pants are each folded twice in the longitudinal direction.

9. The package of claim 8 wherein the first, second, and third pants are each folded three times in the longitudinal direction.

10. The package of claim 6 further comprising a fifth pant, the fifth pant extending substantially the entire height of the housing portion, the fifth pant positioned within the housing portion such that the fifth pant is neither visible through the front transparent window nor visible through the back transparent window.

11. The package of claim 6 wherein each pant defines a crotch region comprising an absorbent composite and being substantially free of elastically transversely gathered portions, and wherein each pant further defines a waist region comprising elastically transversely gathered portions,
    wherein the crotch region of each of the first and second pants is visible through the front transparent window, wherein the crotch region of the fourth pant is visible through the back transparent window, and wherein the waist region of each of the first and second pants is not visible through the front transparent window.

12. A package of disposable absorbent pants, the package comprising:
a housing portion which defines a height and comprises a front panel extending in a front panel plane and a back panel extending in a back panel plane, the front panel plane being substantially parallel to the back panel plane, the front panel comprising a front transparent window;
a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, and each pant comprising elastically transversely gathered portions;
wherein each of the plurality of pants is folded twice in the transverse direction such that the first and second side portions of each pant are folded over the respective center portion,
wherein at least a first pant, a second pant, and a third pant of the plurality of disposable absorbent pants are stacked within and along the height of the housing portion so as to be visible through the front transparent window, each of the first, second, and third pants being folded in the longitudinal direction such that the first, second, and third pants respectively define first, second, and third pant folded heights;
the package further comprising a fourth pant, the fourth pant defining a fourth height which extends along the height of the housing portion,
wherein the first, second, and third pant folded heights are each approximately one-third of the fourth height.

13. The package of claim 12 wherein the back panel comprises a back transparent window, the fourth pant positioned within the housing portion to be visible through the back transparent window.

14. The package of claim 13 wherein the first, second, and third pants are each folded twice in the longitudinal direction.

15. The package of claim 14 wherein the first, second, and third pants are each folded three times in the longitudinal direction.

16. The package of claim 15 wherein fourth pant is folded between one and two times in the longitudinal direction.

17. The package of claim 13 further comprising a fifth pant, the fifth pant defining a fifth height which extends along the height of the housing portion, the fifth pant positioned within the housing portion such that the fifth pant is neither visible through the front transparent window nor visible through the back transparent window, wherein the first, second, and third pant folded heights are each approximately one-third of the fifth height.

18. The package of claim 12 wherein neither the waist end nor the crotch end of any of the first, second, and third pants is visible through the front transparent window.

19. The package of claim 12 wherein no elastically transversely gathered portions of any of the first, second, or third pants are visible through the front transparent window.

20. A package of disposable absorbent pants, the package comprising:
a housing portion and a hanger portion positioned outside of the housing portion, the housing portion defining a height and comprising a front panel extending in a front panel plane and a back panel extending in a back panel plane, the front panel plane being substantially parallel to the back panel plane, the front panel comprising a front transparent window and the back panel comprising a back transparent window;
a plurality of disposable absorbent pants disposed within the housing portion, each pant defining a waist opening, two leg openings, a waist end, and a crotch end, each pant defining both a longitudinal direction that extends from the waist end to the crotch end and a transverse direction that is perpendicular to the longitudinal direction, each pant further defining first and second side portions and a center portion positioned transversely between the first side portion and the second side portion, and each pant comprising elastically transversely gathered portions;
wherein each of the plurality of pants is folded twice in the transverse direction such that the first and second side portions of each pant are folded over the respective center portion;
wherein at least a first pant, a second pant, and a third pant of the plurality of disposable absorbent pants are stacked within and along the height of the housing portion so as to be visible through the front transparent window, each of the first, second, and third pants being folded three times in the longitudinal direction such that the first, second, and third pants respectively define first, second, and third pant folded heights;
the package further comprising a fourth pant, a fifth pant, and a sixth pant, each of the fourth, fifth, and sixth pants being folded one time in the longitudinal direction such that the fourth, fifth, and sixth pants respectively define fourth, fifth, and sixth pant folded heights;
wherein the first, second, and third pant folded heights are each approximately one-third of the fourth pant folded height, are each approximately one-third of the fifth pant folded height, and are each approximately one-third of the sixth pant folded height,
wherein the first, second, and third pants are positioned within the housing portion to be visible through the front transparent window, such that neither the waist end nor the crotch end of any of the first, second, and third pants is visible through the front transparent window,
wherein the fourth pant is positioned within the housing portion to be visible through the back transparent window.

21. The package of claim 20, wherein the first pant and the fourth pant exhibit a first color or first printed pattern, the second pant and the fifth pant exhibit a second color or second printed pattern, and the third pant and the sixth pant exhibit a third color or third printed pattern,
wherein the first color or first printed pattern is visually different from the second color or second printed pattern, wherein the second color or second printed pattern is visually different from the third color or third printed pattern, and wherein the third color or third printed pattern is visually different from the first color or first printed pattern.

22. The package of claim 21, wherein the second pant is sandwiched between the first pant and the third pant, and wherein the fifth pant is sandwiched between the fourth pant and the sixth pant.

* * * * *